(12) United States Patent
Shetty et al.

(10) Patent No.: US 7,897,388 B2
(45) Date of Patent: Mar. 1, 2011

(54) GROWTH OF NEURAL PRECURSOR CELLS USING UMBILICAL CORD BLOOD SERUM AND A PROCESS FOR THE PREPARATION FOR THERAPEUTIC PURPOSES

(75) Inventors: Prathibha Shetty, Maharashtra (IN); Chandra Viswanathan, Maharashtra (IN)

(73) Assignee: Reliance Life Sciences Pvt. Ltd., Rabale, Navi Mumbai, Maharashtra (IN)

( * ) Notice: Subject to any disclaimer, the term of this patent is extended or adjusted under 35 U.S.C. 154(b) by 109 days.

(21) Appl. No.: 11/981,393

(22) Filed: Oct. 31, 2007

(65) Prior Publication Data

US 2008/0124701 A1    May 29, 2008

Related U.S. Application Data

(63) Continuation-in-part of application No. 10/413,356, filed on Apr. 14, 2003, now abandoned.

(30) Foreign Application Priority Data

Apr. 16, 2003    (IN) .................................... 196212

(51) Int. Cl.
*C12N 5/00* (2006.01)
*C12N 5/071* (2006.01)
*C12N 5/074* (2006.01)
*C12N 5/078* (2006.01)
*C12N 5/0789* (2006.01)

(52) U.S. Cl. .................. 435/377; 435/325; 435/366; 435/368; 435/372; 435/404

(58) Field of Classification Search .............. None
See application file for complete search history.

(56) References Cited

U.S. PATENT DOCUMENTS

| | | | |
|---|---|---|---|
| 5,411,883 A * | 5/1995 | Boss et al. ............... 435/29 |
| 6,475,483 B1 * | 11/2002 | Steinman et al. ......... 424/93.7 |
| 7,098,027 B2 * | 8/2006 | Honmou et al. .......... 435/325 |
| 7,160,724 B2 * | 1/2007 | Sanberg et al. .......... 435/377 |
| 2002/0164794 A1 * | 11/2002 | Wernet .................... 435/372 |
| 2003/0039952 A1 * | 2/2003 | Peled ....................... 435/2 |

OTHER PUBLICATIONS

Tondreau et al., Stem Cells, vol. 23, Issue 8, pp. 1105-1112, (2005.).*

* cited by examiner

*Primary Examiner*—Gary B. Nickol
*Assistant Examiner*—Daniel C Gamett
(74) *Attorney, Agent, or Firm*—J. Harold Nissen; Lackenbach Siegel, LLP

(57) ABSTRACT

This invention is concerned with stem cells derived from umbilical cord blood serum and a method for growing human embryonic stem cells and adult cells comprising sera separated from clotted umbilical cord blood, including growing and differentiating cord blood stem cells into neural precursors, comprising transdifferentiating CD34+, CD45+ and CD133+ stem cells from mononuclear cells derived from umbilical cord blood to neural precursors. The stem cells obtained from the umbilical cord include pluripotent stem and progenitor cell population of mononuclear cells, and separating pluripotent stem and progenitor cell population of mononuclear cells obtained from the umbilical cord blood. A magnetic cell separator is used to separate out cells which contain a CD marker and then expanding the cells in a medium containing retinoic acid as a differentiating agent supplemented with one or more growth factors BDNF, GDNF, NGF and FGF in presence of cord blood serum. The invention is also concerned with the transplantation and repair of nerve damage, strokes, spinal injury, Parkinson's and Alzheimer's, prepared with a media for culturing umbilical cord blood stem cells in umbilical cord serum.

9 Claims, 6 Drawing Sheets

FBS CBS

Figure 1: Morphology of cord blood cells cultured in the presence of FBS and CBS

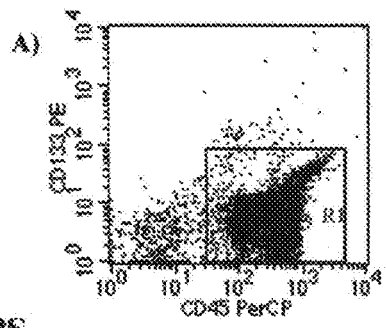
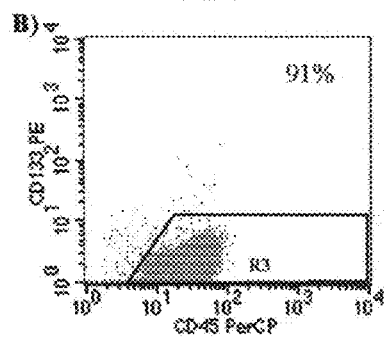
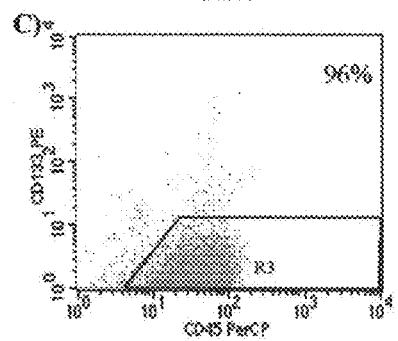
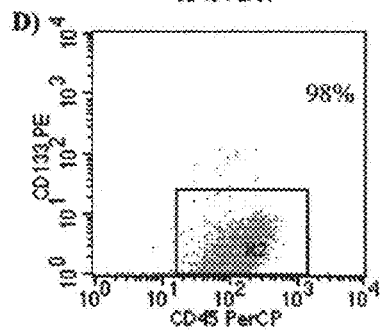
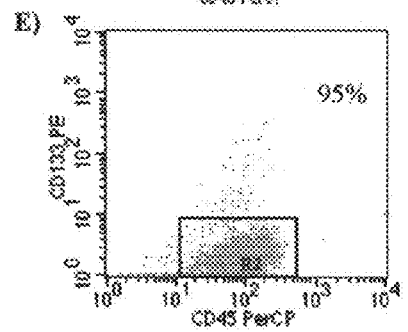
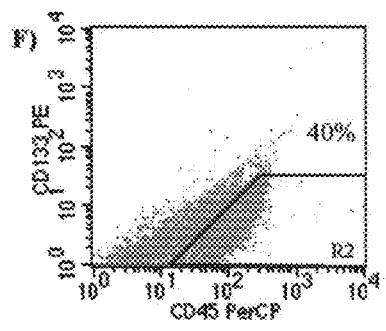
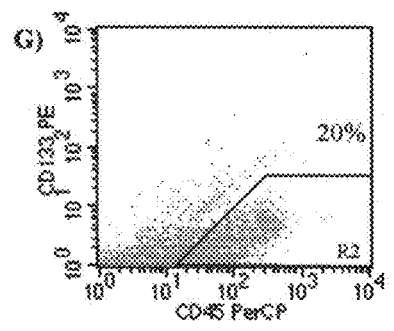
Figure 2: Phenotype of cord blood cells cultured in the presence of FBS and CBS

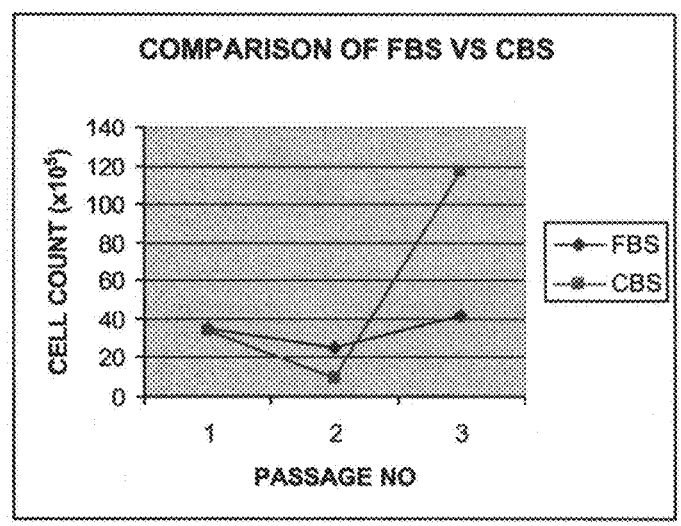
Figure 3: Comparison of the the kinetics CBS Vs FBS

Figure 4: Morphology of the CD133+ cells

4A:- CD133+ cells from cord blood cultured in proliferation medium showed adhered cells, which had a fibroblast, like morphology.

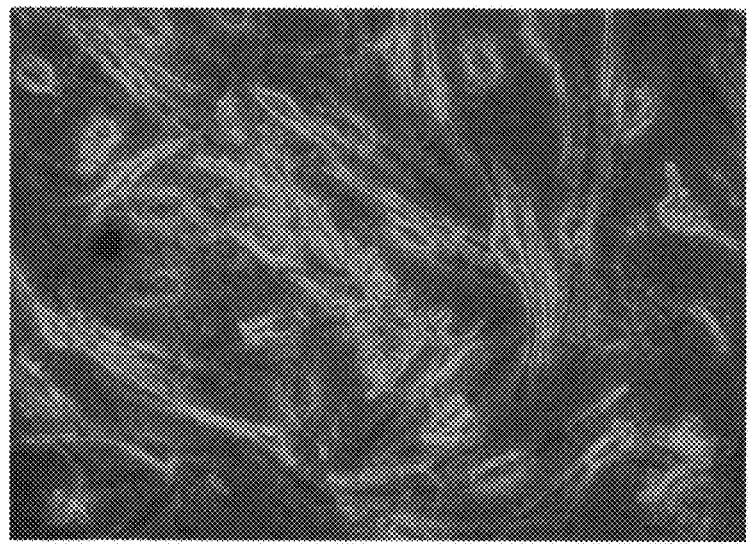

Figure 4B: CD133+ cells cultured in proliferation medium showed fibroblast like upon induction with BHA and All Trans retinoic acid these adhered cells showed a morphology which resembled that of neural cells

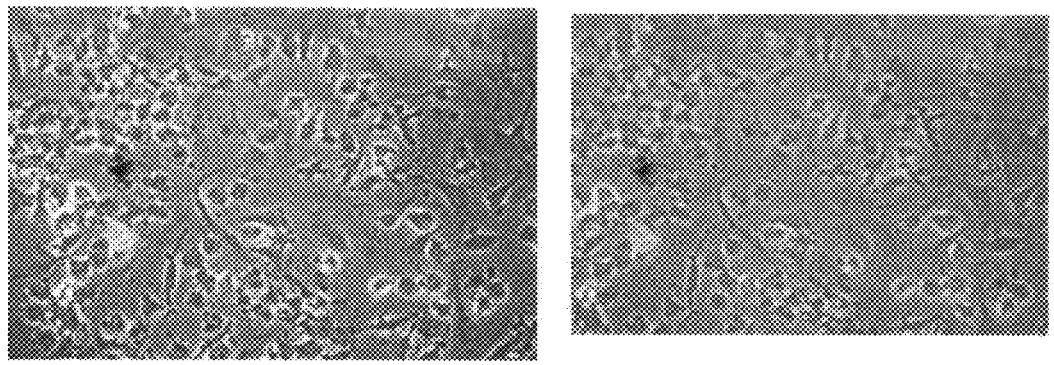

Figure 5: CD133 neural transdifferentiation

5A: Nestin is an intermediate protein and well known specific neural stem cell marker expressed by gliomas & gliobastomas. Of these cells 32% were positive for Nestin.
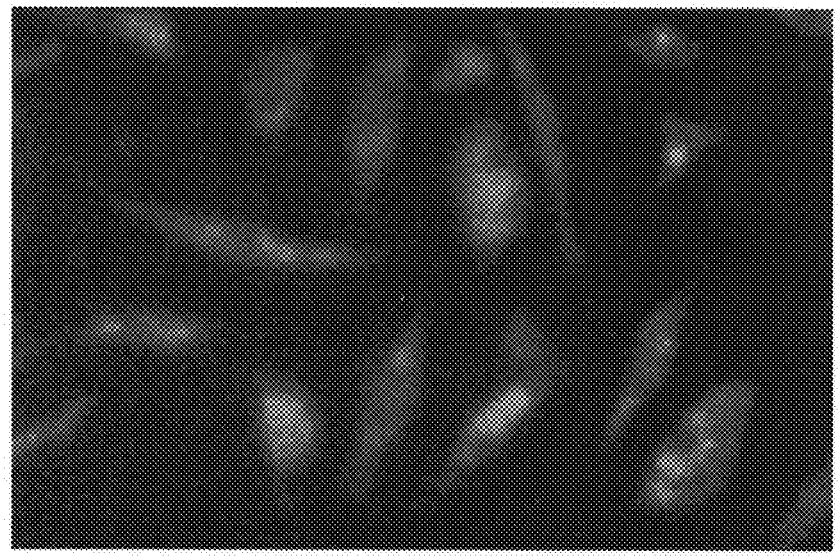
5B GFAP is an astrocytic & glial cell markers expressed by Schwann cells, satellite cells and some groups of ependymal cells
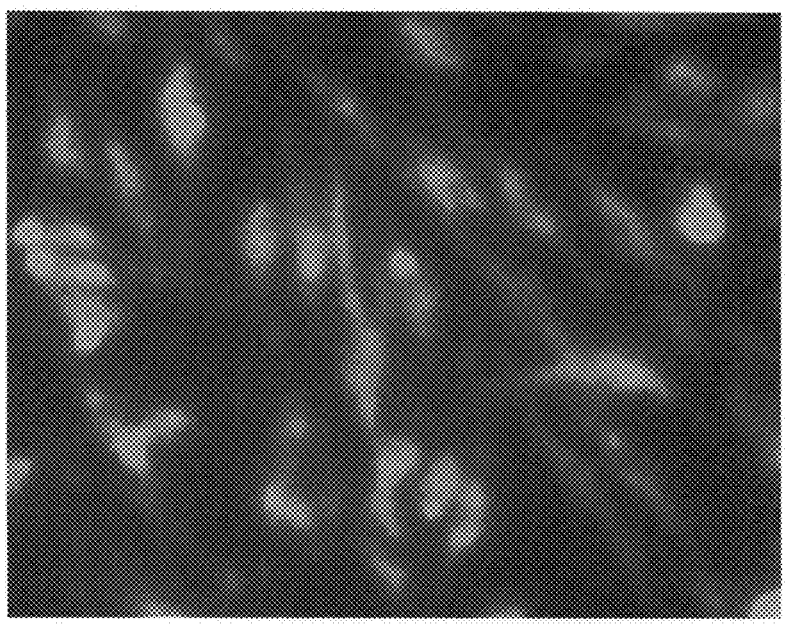

Figure 5C: NeuN is expressed by mature neurons. 30-50% of the differentiated cells expressed NeuN
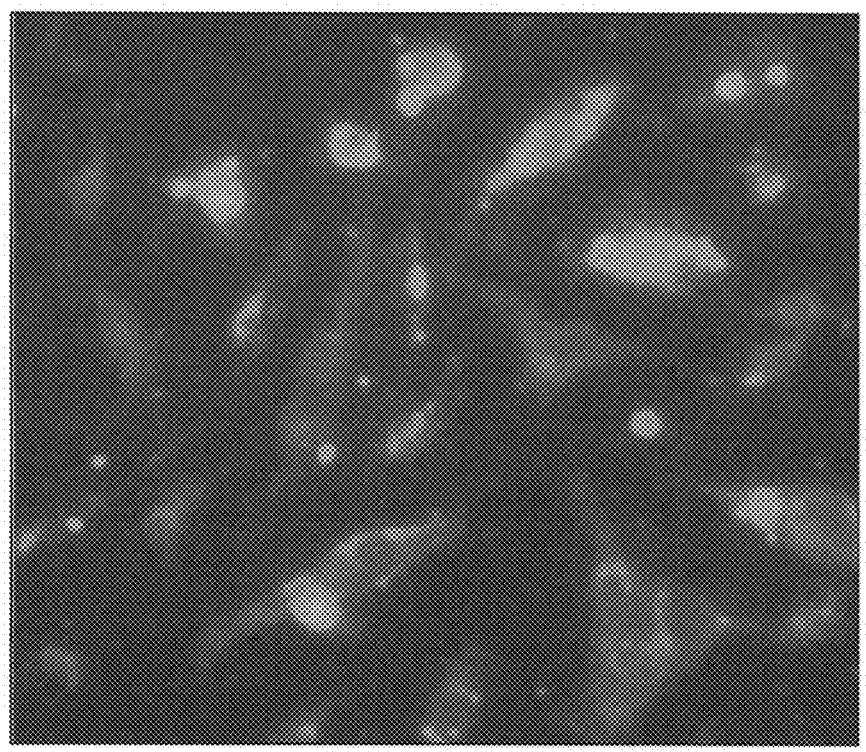
Figure 6: The viability of the cells was checked by viaprobe (7 Amini Actinomycin D). It is based on the dye exclusion property by the dead cells. More than 90% of the cells were viable.
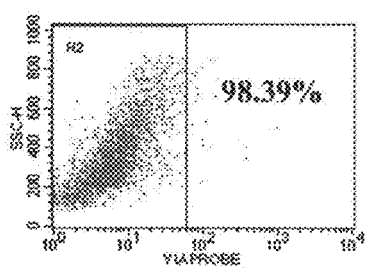

GROWTH OF NEURAL PRECURSOR CELLS USING UMBILICAL CORD BLOOD SERUM AND A PROCESS FOR THE PREPARATION FOR THERAPEUTIC PURPOSES

CROSS REFERENCE TO RELATED APPLICATION

This application is a Continuation in part of U.S. patent application Ser. No. 10/413,356, filed on Apr. 14, 2003, and also claims the priority from Indian Patent Application Serial No. 196212, filed on Apr. 16, 2003 in India.

TECHNICAL FIELD

The present invention provides for the use of sera separated from the clotted umbilical cord blood for growing human embryonic stem cells and adult cells such as Neural precursor cells, for therapeutic purposes in regenerative medicine. In particular, the present invention relates to transdifferentiation of CD+ 34, CD45− and CD133+ stem cells from Mononuclear cells derived from Umbilical Cord Blood to Neural precursors and such cells may be used in transplantation and repair of nerve damage, stroke, spinal injury, Parkinson's and Alzheimer's.

BACKGROUND OF THE INVENTION

Stem cell technology is an emerging field that may yield many promising therapies. Stem cells are special cells that have the ability to develop into many different types of tissue, such as bone, muscle, nerve, etc. In theory, they could be grown into replacements for almost any part of the human body. Stem cells are typically found in the embryo and umbilical cord of an organism, and in reservoirs within the human body. Researchers hope that stem cells will provide a solution to cure diseases caused by cell failure, and for repairing tissues that do not repair themselves. Heart damage, spinal cord injuries, Parkinson's disease, leukemia, and diabetes are among diseases named in relation to stem cell research. Hence, researchers are of the opinion, that if these stem cells are controlled, they could cure a variety of debilitating diseases in the years to come.

Stem cells are separated into three distinct categories viz. Totipotent, Pluripotent, and Multipotent. Stem cells are best described in relation to normal human development. Thus, a fertilized egg is totipotent; a fertilized egg produces an entire organism. After several cycles of cell division, these totipotent cells begin to specialize, becoming pluripotent. As the embryo begins to develop, these pluripotent cells become multipotent, specifically producing blood, skin, nerve, or other types of body cells. Multipotent stem cells are envisioned to potentially treat a variety of muscular-skeletal and neural disorders. While stem cells are extraordinarily important in early human development, multipotent stem cells are also found in children and adults. For example, one of the best understood stem cells are the blood stem cells. Blood stem cells reside in the bone marrow of every child and adult, and in fact, they can be found in very small numbers circulating in the blood stream. Blood stem cells perform the critical role of continually replenishing the supply of blood cells—red blood cells, white blood cells, and platelets throughout the life span.

Stem cells are the building blocks of blood and immune systems. They form the white cells that fight infection, the red cells that carry oxygen and the platelets that promote clotting. Stem cells are normally found in bone marrow where they continue to generate new blood cells throughout the life span of an individual. The presence of these stem cells in the bone marrow has made marrow transplantation an important therapeutic modality in the treatment of a variety of malignant and non-malignant diseases. This is because of the realization that permanent clinical benefit from transfused blood cells can come from transplantation of multipotent haematopoietic stem cells. Besides bone marrow, Mobilized Peripheral Blood (MPB), and Umbilical Cord Blood (UCB) have also been used successfully for transplantation. In recent years although significant advances have been made in bone marrow transplantation (BMT), the basic problem of finding a suitable matching donor still remains. This is because a group of antigens expressed by the leukocytes called the human leukocyte antigens (HLA) need to match between the donor and the recipient. Further bone marrow harvesting is a painful and invasive procedure and many donors are unwilling to donate marrow. Therefore, the search for alternate sources of stem cells has led to the development of stem cell transplant protocols from different tissues like liver (Kochupillai 1991), mobilized peripheral blood (Benboubker 1995), and cord blood (Mayani 1998). Of these, cord blood has significant advantages over the others. Increasingly, experts say cord blood transplants have distinct advantages over more traditional bone marrow transplants in stimulating the growth of healthy white blood cells. Stem cells can be collected from the bone marrow. However, the collection procedure is invasive, time-consuming, requires an anaesthetic and is painful for the donor. Also, cord blood is easily available, involves a non-invasive collection procedure and is better tolerated in transplants across the HLA barrier.

Like bone marrow, umbilical cord blood is rich in stem cells. Umbilical cord blood is the blood that remains in the placenta and umbilical cord following birth. Until recently the placenta and umbilical cord were discarded after delivery as medical waste, but now research has shown that cord blood is a rich source of blood (haematopoietic) stem cells, which can be collected, processed and frozen for potential future use. An experimental procedure to use umbilical cord blood instead of bone marrow to treat immune diseases is gaining attention from doctors and patients.

Research in human developmental biology has led to the discovery of human stem cells (precursor cells that can give rise to multiple tissue types), including embryonic stem (ES) cells, embryonic germ (EG) cells, fetal stem cells, and adult stem cells. Recently, techniques have been developed for the in vitro culture of stem cells, providing unprecedented opportunities for studying and understanding human embryology. As a result, scientists can now carry out experiments aimed at determining the mechanisms underlying the conversion of a single, undifferentiated cell, the fertilized egg, into the different cells comprising the organs and tissues of the human body. Although it is impossible to predict the outcomes, scientists and the public will gain immense new knowledge in the biology of human development that will likely hold remarkable potential for therapies and cures.

Using cell replacement therapy, to cure diseases may prove to be one of the most significant advances in medicine. Unlike all current treatments that rely on surgical interventions or drugs that modulate cell activities, stem cells provide a replacement for dysfunctional or degenerating tissue.

Cell implantation offers hope for actually replacing nerve cells lost in Parkinson's and many other neurological diseases. Using cell replacement therapy, to cure diseases may prove to be one of the most significant advances in medicine. Unlike all current treatment that relies on surgical interventions or drugs that modulate cell activities, stem cells provide a replacement for dysfunctional or degenerating tissue. Clinical trials of fetal tissue transplantation, still underway, have developed methods for implanting cells into the brain and demonstrated the viability of the concept and promising results for at least some patients. One of the major problems in the cell transplantation is the need of large number of neuronal cells.

Cells are regarded as stem cells if they retain the capacity to renew themselves as well as more specialized progeny. Stem cells can be obtained from early embryo, fetal tissues, adult blood, and umbilical cord blood. Identification of the full term umbilical cord blood (which is discarded at birth), as a source has made haematopoietic stem cells more accessible for study and clinical use. Cord blood stem cells are multipotent. These stem cells in addition to the production of blood cells, have the ability to differentiate into cells of other tissue or organs. This ability has made cord blood stem cells more accessible for study and clinical use.

Umbilical cord blood is typically depleted of RBC and the leukocyte rich fraction is subjected to density gradient separation to yield mononuclear cell fraction (MNC).

Typically MNCs comprise hematopoietic and non haematopoietic cells. The haematopoietic cells further comprises monocytes and lymphocytes.

Cord blood stem cells express are multipotent. These stem cells in addition to producing blood cells have the ability to differentiate into cells of other tissue or organs. This ability has made cord blood stem cells more accessible for study and clinical use. Umbilical cord blood is rich in many stem cells including haematopoietic precursors and therefore represents a good source of cells for haematopoietic reconstitution. However, little work has been done using stem cells or neuronal precursors found in umbilical cord blood for neural transplantation. Published U.S. Patent Application Serial No. 2002/0028510 A1 describes the use of cord blood mononuclear cells for treating neural disorders. In this patent publication, the cord blood mononuclear cells are differentiated into neuronal and glial cells using Fetal Bovine Serum (FBS). The scientists of the present invention have developed an improved method for growth and differentiation of the cord blood mononuclear cells. In the present invention, cord blood mononuclear cells are grown and differentiated into neural cells using human umbilical cord blood serum. Since the present invention uses human umbilical cord blood serum, the risks associated with the use of FBS are circumvented, thereby improving the engrafting ability of the cells.

Cord blood stem cells express CD34 antigen. CD 34 antigen has been commonly used as a marker for the enrichment and isolation of candidate stem cells. Cord blood stem cells can be isolated on the basis of the presence of this marker. CD34 positive cells can be isolated from mononuclear cells of cord blood. Cord blood mononuclear cells constitute about 1-2% of CD34 positive cells. On exposure to a novel environment, cord blood stem cells are known to transdifferentiate into various cells like neural cells, liver cells, bone, cartilage etc. The CD markers are used to typically select the required type of cells. For example CD 34 is a specific marker for haematopoietic stem cells, CD45 is a specific marker for lymphocytes.

Transdifferentiation is the ability of the adult stem cells from one tissue or organ, which can overcome their intrinsic restrictions upon exposure to novel environment perhaps via genomic reprogramming to cells of other organs either in vitro, or after transplantation in vivo.

Many neurological diseases such as Parkinson's disease, Alzheimer's disease, Multiple sclerosis, Huntington's disease, Amyotrophic lateral sclerosis and Cerebral ischemia including Stroke are characterized by degeneration of neurons in the brain and spinal cord regions. Such neurological diseases result in the loss of neurons and these degenerated cells or neurons are not intrinsically replaced or repaired (During et al. 2001).

There is substantial evidence in both animal models and human patients that neural transplantation is a scientifically feasible and clinically promising approach to the treatment of neurological diseases and stroke, as well as for repair of traumatic injuries to brain and spinal cord. Nevertheless, alternative cell sources and novel strategies for differentiation are needed to circumvent the numerous ethical and technical constraints that now limit the widespread use of neural transplantation.

Neural stem cell research is still in its early stages, is intriguing because scientists believe that the primitive cells can transform into virtually any cell type in the body and could be a source of tissue or organs to cure diseases such as repair of nerve damage, strokes, spinal injury, Parkinson's and Alzheimer's. For years, researchers studying stem cells have been intrigued by the possibility that these cells might be useful to treat brain diseases. Recent studies have suggested neural stem cells transplanted into the brain can migrate throughout the brain and develop into other types of cells.

Up to the present, Stem Cells (Embryonic/Adult) are being cultured in animal serum such as Fetal Bovine Serum (FBS), or a complex mixture of growth factors derived by mixing purified factors which are either isolated from FBS or Human Adult blood serum or a mixture of growth factors derived from recombinant methods. However, these conventional culture media are associated with shortcomings and risks.

Stem cells from adult/fetal as well as other sources are being widely used to regenerate tissues in patients after they have degenerated. For this purpose, these cells have to be grown in the tissue culture for varying periods of time using defined media, the principle constituent of which is animal serum such as Fetal Bovine Serum (FBS).

However, these conventional culture media are associated with shortcomings and risks. Stem cells from adult/fetal as well as other sources are being widely used to regenerate tissues in patients after they have degenerated. For this purpose, these cells have to be grown in the tissue culture for varying periods of time using defined media, the principle constituent of which is animal serum such as Fetal Bovine Serum (FBS).

FBS is the most widely used serum in the culturing of cells, tissues and organs in vitro, in industry, medicine, and science. FBS has been shown to be essential for adhesion, proliferation and differentiation of the cells. However, animal serum such as FBS can be infected with several pathogens such as prions. Several known and unknown viruses may be present in the serum. Therefore cells/tissue cultured in the presence of FBS get infected and transmit these pathogens to the patient on transplantation. As stated FBS may have known and unknown pathogens, which may be transmitted to the human transplant subject if these cells are grown in FBS. The pathogens present in FBS are difficult to screen for likely causative agents of diseases in humans. Hence, using such cells in a human can be life threatening as there is every chance of a pathogen getting transmitted along with these cells. Human cells grown in FBS constitute a xenograft, if used for cells based therapies in humans.

Human adult blood serum also supports growth of several cells, however, it cannot substitute for FBS, since it does not provide growth factors, present in FBS. Hence, it is not used for culturing of stem cells in vitro.

Several investigators have tried to use a combination of complex mixture of growth factors, which are known to influence growth and differentiation of stem cells. However, the success is limited and it has been shown conclusively that 2% v/v of the tissue culture media should be made up of FBS for optimal growth of the cells.

There is a dire need to find an adequate substitute for conventional culture media for growing neural precursor cells. Looking to the need of the hour, the present inventors have resolved the above issue of concern and have come out with a solution, which will be of utmost importance in the field of regenerative medicine. The inventors of the present invention, have come out with a unique media for culturing cord blood stem cells which comprises umbilical cord blood serum as a substitute for FBS and such cells may be used in transplantation and repair of nerve damage, strokes, spinal injury, Parkinson's and Alzheimer's. Cord blood being a natural substance, is found to be rich in growth factors. Taking this factor in mind, the inventors of the present invention have investigated a method of growing and differentiating cord blood stem cells into neural precursors. The present invention is advantageous over the prior art as it obviates the problems associated with the conventional culture media for growing stem cells for human use.

Use of umbilical cord blood stem cells in haematopoietic reconstitution has been around since 1970.

U.S. Pat. No. 7,160,723 to Sanberg et al. has provided the source of neural precursors from umbilical cord blood. They have depleted RBC, and the MNC fraction is then subjected to a selection of Non hematopoietic cells and these Non hematopoietic cells are then differentiated in a medium that allows the cells to become neural cells.

U.S. Pat. No. 7,160,724 to Sanberg et al. has provided the source of neural precursors from umbilical cord blood. They have depleted RBC, and the MNC fraction is then subjected to a selection of Non haematopoietic cells and these Non haematopoietic cells are then differentiated in a medium that allows the cells to become neural cells.

The inventors of the present invention have been successful in discovering this novel process for growing cord blood stem cells and differentiating the cord blood stem cells into neural precursors. More particularly, the present invention derives the neural precursors from the lymphocyte portion of haematopoietic progenitors of the mononuclear cell fraction of umbilical cord blood.

OBJECTS OF THE INVENTION

It is an object of the present invention to develop a method for growing and differentiating stem cells into neural precursors using a novel media consisting of cord blood serum, and such cells may be used in transplantation and repair of nerve damage, stroke, spinal injury, Parkinson's and Alzheimer's.

It is another object of the present invention to derive the neural precursors from the lymphocyte portion of haematopoietic progenitors of the mononuclear cell fraction of umbilical cord blood by way of selection of the cells using CD marker.

It is a further object of the present invention to isolate the CD34+ cells which is the haematopoietic cells of the Mononuclear cell fraction.

It is a still further object of the present invention to expand the CD34+ cells in a proliferation medium and analyze the cells until they become CD34+ CD45− and CD 133+.

It is a still further object of the present invention to transdifferentiate CD34+, CD 45− and CD 133+ stem cells from Mononuclear cells derived from Umbilical Cord blood to neural precursors.

It is also an object of the present invention to develop a method for growing and differentiating stem cells derived from umbilical cord blood into neural precursors using a novel media consisting of cord blood serum, and such cells may also be used in transplantation and repair of nerve damage, stroke, spinal injury, Parkinson's and Alzheimer's.

It is a still further object of the present invention to replace conventionally used media containing fetal media bovine serum as a growth supplement by cord blood serum of the present invention, for culturing cord blood stem cells for neural transdifferentiation.

SUMMARY OF THE INVENTION

In accordance with one aspect of this invention, there is provided the use of umbilical cord blood sera for growing human embryonic stem cells and adult cells, like cord blood stem cells for therapeutic purposes in regenerative medicine.

Another aspect of this invention is that there is provided a method for the growth and differentiation of umbilical cord blood stem cells into neural precursor cells using cord blood sera.

To overcome the major obstacle described above, the inventors of the present invention have conducted research on human umbilical cord blood and have replaced conventionally used Fetal Bovine Serum (FBS) by cord blood serum, for culturing cord blood stem cells for neural transdifferentiation.

The present invention describes the use of umbilical cord blood serum for culturing cord blood mononuclear cells or pluripotent stem cells/progenitor cells.

As stated, Human umbilical cord blood is a fetal product and a waste product during childbirth. During the gestation of the child in the mother's womb, the placenta and the blood present in the placenta nourish the developing fetus and are therefore rich in several growth promoting factors. The inventors of the present invention have taken advantage of this property of Human umbilical cord blood and have substituted it for FBS. The procedure by which Human umbilical cord blood is collected is given below. It is this cord blood that is used as a serum for growing cord blood stem cells of the present invention.

The method of the present invention may include the step of separating the pluripotent stem and progenitor cell population of mononuclear cells obtained from umbilical cord blood using a magnetic cell separator to separate out cells which contain a CD marker and then expanding these cells in a growth medium containing a differentiation agent such as retinoic acid and growth factors such as BDNF, GDNF, NGF, FGF or mixtures thereof.

Preferably, a mixture of retinoic acid and at least one growth factor for example nerve growth factor is used as the differentiation agent. The retinoic acid may be 9-cis retinoic acid, all-trans retinoic acid or mixtures thereof. The separation and incubation steps maybe interchanged.

The umbilical cord blood sample from which the pluripotent stem/progenitor cells are obtained may be fresh umbilical cord blood, reconstituted cryopreserved umbilical cord blood or a fresh or reconstituted cryopreserved mononuclear cell fraction thereof.

The process of the present invention involves the RBC depletion of the umbilical cord blood (UCB), further subjected to density gradient separation to isolate the mononuclear fraction (MNC's). This MNC fraction is subjected to CD marker selection by MACS especially CD 34+ cells which are also CD133+. The selected CD34+ and CD133+ cells were grown in neural proliferation media comprising umbilical cord blood serum. The proliferated cells were analyzed for CD34+, CD45– and CD133+. The analyzed cells were then transdifferentiated in media comprising retinoic acid and BHA as differentiating agent and bFGF and umbilical cord blood serum to give neural precursors.

These cells are differentiated using differentiation agent such as b-Hydroxyanisole (BHA), retinoic acid, dimethyl sulfoxide (DMSO), b-mercaptoethanol and at least one growth factor for example nerve growth factor is used as the differentiation agent.

To these ends, the present invention consists in the provision of neural precursor stem cells derived from mononuclear cells of umbilical cord blood growing in a media comprising: neural proliferation medium which effectively gives proliferated neural cells, followed by growing these proliferated cells in a neural differentiation medium similar to the neural proliferation medium with additional neural differentiation agents in presence of cord blood serum, and which cells can be further differentiated into a variety of neural phenotypes used for regenerative medicine like transplantation and repair of nerve damage, strokes, spinal injury, Parkinson's and Alzheimer's Diseases and/or cell based therapies, and the stem cells being derived from stem cells grown in a neural proliferation medium, and then these proliferated cells are grown in a neural differentiation medium in the presence of cord blood serum.

The invention also contemplates the provision of neural precursor stem cells derived by growing neural precursor cells from umbilical cord blood for regenerative medicine, comprising the steps of:

i. isolating stem cell and progenitor cell population from mononuclear cells separated from umbilical cord blood, using a magnetic cell separator to separate out cells which contain a CD marker;

ii. culturing the stem cell and progenitor cell population of step (i) in a culture vessel, using a neural proliferation medium containing cord blood serum in a $CO_2$ incubator;

iii. feeding the cultures of step (ii) every 3-4 days and allowing them to proceed to 90% confluency;

iv. detaching adherent cells attached to the culture vessel using cell dissociation buffer or trypsin EDTA or any such dissociation agent and seeding into the next passage;

v. characterizing cultured cells of step (iv) by taking cell counts and analyzing these cells for the expression of CD133, CD45 and CD34 marker; and vi. transdifferentiating these cells in a neural differentiation media.

Another feature of the invention is directed to the method of growing mononuclear cells into neural precursors comprising the steps of using a selection marker to isolate the mononuclear cells from the umbilical cord blood and growing these selected cells in a neural proliferation media, analyzing the proliferated cells and further growing the proliferated cells in a neural differentiation media comprising differentiation agents to provide neural precursors wherein the media comprises cord blood serum.

The invention is also directed to a method of using umbilical cord blood serum for growing the mononuclear cells from umbilical cord blood into neural precursors for therapeutic purpose in regenerative medicine comprising:

a) collecting the umbilical cord blood;

b) isolating the mononuclear cell fraction from the umbilical cord blood;

c) separating pluripotent stem and progenitor cell population of mononuclear fraction from umbilical cord blood using a magnetic cell separator to isolate the CD34+, CD45+ and CD133+ cells;

d) culturing the isolated cells in a neural proliferation medium comprising cord blood serum;

e) analyzing for CD34–, CD45– and CD133+ cells; and f) further transdifferentiating these proliferated cells in a neural differentiation medium to neural precursors.

The invention is also concerned with a method of growing mononuclear cells into neural precursors comprising steps of using selection markers CD34, CD45, and CD133 to isolate the mononuclear which are CD34+, CD45–, and CD 133+ from the umbilical cord blood and growing these cells in a neural proliferation media, analyzing the proliferated cells for CD34–, CD45– and CD133+ and further growing these proliferated cells in a neural differentiation media comprising differentiation agents to provide neural precursors wherein the media comprises cord blood serum.

BRIEF DESCRIPTION OF THE FIGURES

FIG. 1: generally shows the morphology of adherent cells grown in the presence of FBS and CBS and includes FIGS. 1A, 1B, 1C and 1D. In the first passage (P1) higher numbers of adherent cells are observed in the CBS culture shown in FIG. 1B. In FIGS. 1C and 1D, a similar difference is observed in cultures in the second passage (P2). The adherent cells in CBS also appear to be larger in size. FIG. 1C shows the larger size FBS cells, and FIG. 1D shows the larger size of adherent cells in CBS.

FIG. 2: shows the flow cytomteric analysis of cord blood cells cultured in the presence of FBS and CBS. In P1 and P2 of both the groups, FBS and CBS, are cultures >90% of the cells exhibit a CD133– and CD45+ phenotype. FIG. 2A shows the CD45 profile of day 0 cells at the initiation of these cultures. FIGS. 2B and 2C show the CD45 profile of cells cultured in the presence of FBS and CBS respectively at Passage 1 (P1). FIGS. 2D and 2E show the CD45 profile of cells cultured in the presence of FBS and CBS respectively at Passage 2 (P2). Similarly FIGS. 2F and 2G show the CD45 profile of cells cultured in the presence of FBS and CBS respectively at Passage 3 (P3). In P1 and P2 cultures of both the groups (FBS and CBS) of the cells exhibit a CD133–/CD45+ phenotype. The regions in these dot plots are drawn on the basis of isotype controls.

FIG. 3: shows a comparison of the kinetics CBS VS FBS.

FIG. 4: shows morphology of the CD133+ cells and includes FIGS. 4A and 4B.

FIG. 4A: shows CD133+ cells from cord blood cultured in a proliferation medium illustrated with adhered cells, which had a fibroblast, like morphology, and FIG. 4B: shows CD133+ cells cultured in a proliferation medium together with a fibroblast like upon induction with BHA and All Trans retinoic acid and these adhered cells illustrate a morphology which resembled that of neural cells.

FIG. 5: shows CD133 neural transdifferentiation, and includes FIGS. 5A, 5B and 5C.

FIG. 5A: shows Nestin which is an intermediate protein and well known specific neural stem cell marker expressed by gliomas and gliobastomas; of these cells 32% were positive for Nestin. FIG. 5B: shows GFAP which is an astrocytic and glial cell markers expressed by Schwann cells, satellite cells and some groups of ependymal cells. FIG. 5C: shows NeuN which is expressed by mature neurons. 30-50% of the differentiated cells expressed NeuN.

FIG. 6: shows the viability of the cells after being checked by viaprobe (7 Amini Actinomycin D); it is based on the dye exclusion property by the dead cells, and more than 90% of the cells were viable.

DETAILED DESCRIPTION OF THE INVENTION

Figure 1A:
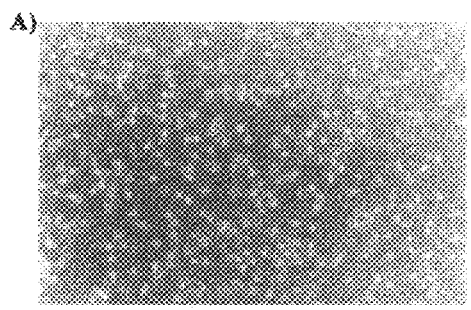

The following terms are used throughout the specification to describe the present invention.

The term "umbilical cord blood" or "cord blood" is used throughout the specification to refer to blood obtained from a neonate or fetus, most preferably a neonate and preferably refers to blood which is obtained from the umbilical cord or placenta of newborns. The use of cord or placental blood as a source of mononuclear cells is advantageous because it can be obtained relatively easily and without trauma to the donor. Cord blood cells can be used for autologous or allogenic transplantation when and if needed. Cord blood is preferably obtained by direct drainage from the umbilical vein.

The term "cell medium" or "cell media" is used to describe a cellular growth medium in which mononuclear cells and/or neural cells are grown. Cellular media are well known in the art and comprise at least a minimum of essential medium plus optional agents such as growth factors, glucose, non-essential amino acids, insulin, transferring and other agents well known in the art. In certain preferred embodiments, at least one differentiation agent is added to the cell media in which a mononuclear fraction is grown in order to promote differentiation of certain cells within the mononuclear fraction into neural cells.

The term "non adherent cells" is used to describe cells remaining in suspension in the tissue culture flask at the end of the culture period. The term "adherent cells" is used to describe cells that are attached to the tissue culture plastic, but are detached from the flask by addition of enzyme free cell dissociation buffer from Gibco-BRL or by addition of trypsin-EDTA.

In the present invention, umbilical cord blood serum is prepared in the following manner. Umbilical cord blood is collected at the time of birth from pre-screened mothers for infectious disease causing organisms, such as HIV 1 and 2, HbsAg and HCV and sexually transmitted diseases. The collection is made after the baby is separated from the clamped cord, and therefore there is no harm to the baby. Blood is collected from an umbilical vein using the conventional blood bag containing no anticoagulants. The needle of the bag is inserted into the vein and blood is allowed to flow into the blood bag. A good collection can exceed 100 ml. This blood is now allowed to clot at room temperature and transported to the processing area, which is a cGMP clean room. The clotting process is allowed to take place from 8-16 hours. The blood is then centrifuged at 1000 g in a blood bag centrifuge and the clear serum is collected into sterile containers. The serum is now tested for sterility by microbiological assays for aerobic or anaerobic microorganisms. The complement is inactivated by keeping sera at 56° C. for ½ hour. Serum is aliquoted into 10 ml sterile vials and capped. Lot number and Batch number are fixed on it.

In a preferred aspect of the present invention, mononuclear cells derived from umbilical cord blood in a conventional manner as grown in a standard cellular media (preferably, at least a minimum essential medium supplemented with non-essential amino acids, glutamine and serum). These cells are grown in a "neural proliferation medium" (i.e. a medium which efficiently grows neural cells) followed by growth in a "differentiation medium," generally which is similar to a neural proliferation medium with the exception that specific neural differentiation agents are added to the neural proliferation medium and in other cases or mediums components are used at a reduced concentration or, certain growth factors are limited or removed.

A particularly preferred neural proliferation medium is a medium which contains DMEM/F12 1:1 cell medium supplemented with glutamine 2 mM, sodium biocarbonate 3 mM, EGF 20 ng/ml, bFGF 10 ng/ml and NGF 100 ng/ml in the presence of cord blood serum and the neural differentiation medium is the neural proliferation medium when added differentiation agents such as retinoic. One of ordinary skill will readily recognize that any number of cellular media maybe used to grow mononuclear cell fractions of umbilical cord blood or to provide an appropriate neural proliferation media and/or differentiation media. A particularly preferred neural differentiation medium is similar to neural proliferation medium with the exception that differentiation agent BHA is added to the medium.

A particularly preferred neural proliferation medium is a medium which contains DMEM/F12 1:1 cell medium supplemented with glutamine 2 mM, sodium biocarbonate 3 mM, EGF 20 ng/ml, bFGF 10 ng/ml and NGF 100 ng/ml in the presence of cord blood serum and the neural differentiation medium is the neural proliferation medium when added differentiation agents such as retinoic. One of ordinary skill will readily recognize that any number of cellular media may be used to grow mononuclear cell fractions of umbilical cord blood or to provide an appropriate neural proliferation media and/or differentiation media. A particularly preferred neural differentiation medium is similar to neural proliferation medium with the exception that differentiation agent BHA is added to the medium.

Selecting for umbilical cord blood pluripotential stem/progenitor cells according to the present invention can be done in a number of ways. For example, the cells may be selected using, for example a magnetic cell separator (MACS) or other system which removes all the cells which contain a CD marker and then the remaining cells may be expanded in a growth medium or differentiated in a growth medium which includes a differentiation agent.

Alternately, cells expressing some markers like CD 133 can also be isolated and expanded in growth medium followed by differentiation in differentiation medium.

Additional in vitro differentiation techniques can be adapted through the use of various cell growth factors and co-culturing techniques known in the art. Besides co-culturing with adult mesenchymal stem cells, a variety of other cells can be used, including but not limited to accessory cells and cells from other portions of the fetal and mature central nervous system.

The following written description provides exemplary methodology and guidance for carrying out many of the varying aspects of the present invention.

Enrichment of mononuclear cells is well known to the practitioners of the art. Briefly, red blood cell depletion is carried out using 3% v/v Dextran (high molecular weight) in the ratio of 1:1 with respect to the volume of blood. Leucocyte rich plasma is collected carefully and centrifuged. Cells are washed and layered on Histopaque™ 1077 or FICOLL. The tubes containing the sample are centrifuged at 400 g for 30 minutes. Mononuclear cells are separated from the interface using pipettes. These cells are washed and counted. The mononuclear cells are then suspended in a neural proliferation medium. Mononuclear cells may also be subjected to MACS isolation for enriching stem cells and progenitor cells and then suspended in neural proliferation medium.

On culturing in media comprising umbilical cord blood serum wherein the non adherent cells were taken for counting and analyzing and further differentiation. The cells are also stained with fluorochrome conjugated antibodies for flow cytometry. Specified numbers of cells are taken in polystyrene round bottom tubes. These cells are then stained with anti-CD34-FITC, anti-CD133-PE and anti-CD45-PerCP antibodies. The stained cells are then acquired and analyzed on a FACSCalibur flow cytometer.

The Applicant has achieved better proliferation kinetics than that grown in fetal bovine serum and that it was morphologically similar.

Further with the addition of neural differentiation agents, the Applicant has achieved either the disappearance of or a low count of CD34 haematopoietic and CD 45 (hymphocytes) and a high count of CD133 (neural marker). It should be noted that CD133 is a specific marker for neural stem cells.

EXAMPLES

Example 1

Isolation of the Mononuclear Cell Fraction from Umbilical Cord Blood

The umbilical cord blood was mixed with 3% sterile Dextran in a 1:1 ratio and allowed to stand for 30 minutes at Room temperature. The mixture was shaken intermittently after 30 minutes and again allowed to stand for 30 minutes. The Leukocyte rich plasma (LRP) was collected after RBC sedimentation. The LRP was spun at 1500 rpm for 5 minutes. Subsequently, the supernatant was decanted and the cell pellet was dispersed. The cell pellet was then suspended in sterile PBS and again spun at 1500 rpm for 5 minutes. The supernatant was decanted and the cell pellet thus obtained was then dispersed once again. This leucocyte pellet was then suspended in 35 ml sterile PBS.

For the separation of the mononuclear cells, 35 ml of the cell suspension was suspended in 12 ml Ficoll-Hypaque (density 1,077 gm/dm$^3$). The tube was centrifuged at 1500 rpm for 30 minutes. The buffy coat (which contains the mononuclear cells) at the interface of PBS and Ficoll Hypaque were collected. The cells were suspended in sterile PBS and centrifuged at 1500 rpm for 5 minutes. This density gradient separation was again repeated and finally the cells were suspended in sterile PBS and centrifuged at 900 rpm for 5 minutes. Finally the cells were suspended in 1 ml sterile PBS and the cell count was taken on the Hemocytometer.

Example 2

Effect of Cord Blood Serum on the Proliferation of Non-Adherent Cells

Mononuclear cells from cord blood are plated in Nunc T75 culture flasks in neural cell proliferation medium containing DMEM:F12+10% FBS or 10% CBS, supplements with growth factors such as EGF-20 ng/ml, NGF-100 ng/ml, FGF-10 ng/ml. The cells are seeded at a density of $1 \times 10^6$ to cells/ml. After a fixed culture period of 1 week, the supernatant was collected and centrifuged at 1500 rpm for 5 minutes. Then again the supernatant was decanted and the cell pellet was washed with sterile PBS twice. Subsequently the cell count was done using haemocytometer and $2 \times 10^6$ were stained for flow cytometer (2 tubes, $1 \times 10^6$ per tube).

The suspension cells were stained with Anti Human CD34-FITC antibody, Anti Human CD133-PE.

The non-adherent cells counted and analyzed for the expression of CD133, CD45 and CD34 markers.

Table 1 shows the proliferation kinetics of these cells in this medium. No significant difference (p>0.3) as measured by the paired T test in the numbers of non adherent cells, is observed in cells cultured in the presence of CBS or FBS. This shows that cord blood serum supports growth of non-adherent cells in these cultures with equal efficacy as compared to fetal bovine serum.

TABLE 1

Cell count of non adherent cells from cord blood grown in FBS and CBS Cell count of non adherent cells from cord blood grown in FBS and CBS Sample Cell number (.times.10.sup.6) at P1 no CBS FBS

| Sample | Cell number ($\times 10^6$) at P1 | |
|---|---|---|
| no | CBS | FBS |
| 1 | 2.5 | 2.6 |
| 2 | 2.0 | 4.0 |
| 3 | 3.6 | 4.3 |
| 4 | 16.0 | 11.8 |
| 5 | 0.5 | 0.5 |
| 6 | 1.5 | 1.7 |
| 7 | 8.0 | 1.1 |
| Mean | 4.9 | 3.7 |

No significant difference (p>0.3) as measured by the paired T test in the numbers of non adherent cells, is observed in cells cultured in the presence of CBS or FBS. This shows that cord blood serum supports growth of non-adherent cells in these cultures with equal efficacy as compared to fetal bovine serum. Sample numbers 4 and 7, CBS cultures showed a significantly higher number of non adherent cells as compared to FBS cultures. This may be a peculiarity of the individual cord blood samples, which is not observed in all samples. However, this table does confirm the fact that CBS was able to support good cell growth as compared to FBS.

Example 3

Effect of Cord Blood Serum on the Proliferation of Adherent Cells

Mononuclear cells from umbilical cord blood were plated into a neural cell proliferation medium as described above. The cultures were fed every 3-4 days and were allowed to proceed to 90% confluency, which was determined by visual examination of the flask under an inverted microscope. The adherent cells were initially detached using cell dissociation buffer and seeded into the next passage.

Table-2 shows the numbers of cells detached with cell dissociation buffer in both these cultures. Cultures containing FBS showed a 1.7 fold higher number of adherent cells (p<0.05) as compared to cultures containing CBS. However since an appreciable number of cells were still adherent to the CBS tissue culture flask, it was decided to use trypsin-EDTA instead of cell dissociation buffer for detachment of cells.

Figure 1B:
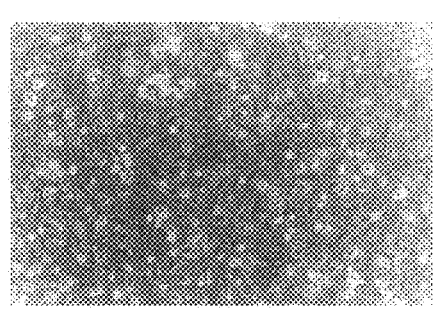
Figure 1C:
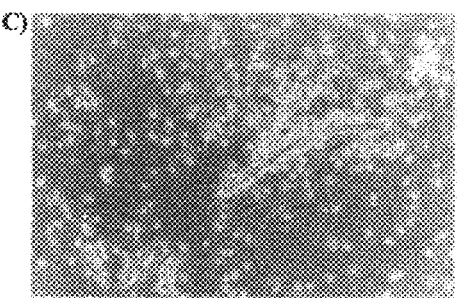
In FIG. 1C, the FBS culture shows a higher number of rounded cells, but lower number of adherent cells.
Figure 1D:
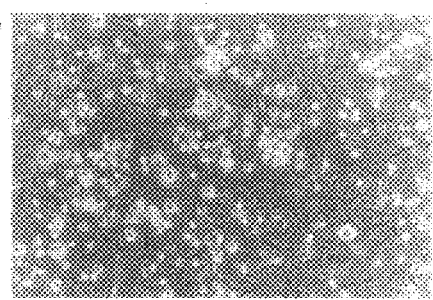

In one experiment where cells were detached using trypsin-EDTA, cultures containing CBS showed a 2 fold higher number of adherent cells compared to the culture containing FBS. This is also clear from FIG. 1.

At each passage an aliquot of the cells was phenotyped by flow cytometry. FIG. 1 shows the morphology of these cells in culture. Although equal numbers of cells were seeded in these cultures the cells in the flask containing CBS appear to be growing at a higher cell density as compared to the flask containing FBS.

TABLE 2

Cell count and phenotype of adhered cord blood cells grown in FBS and CBS
Cell count and phenotype of adhered cord blood cells grown in FBS and CBS % CD133−/CD34−/CD45− Cell number (.times.10.sup.6)(P1) Sample No. CBS FBS CBS FBS

| Sample No. | Cell number (×10$^6$) | | % CD133−/CD34−/CD45+ (P1) | |
|---|---|---|---|---|
| | CBS | FBS | CBS | FBS |
| 1 | 0.3 | 0.5 | — | — |
| 2 | 0.2 | 0.6 | 94.9 | 87.4 |
| 3 | 0.3 | 0.7 | 93.3 | 92.5 |
| 4 | 2.2 | 2.5 | 93.9 | 90.7 |
| 5 | 0.4 | 1.5 | 93.8 | 91.9 |
| Mean | 0.7 | 1.2 | 91.8 | 89.2 |

The morphology of the cells grown in these two cultures is also very different. Cells grown in the presence of CBS have a flattened morphology and are larger in size as compared to cells grown in the presence of FBS. These cells grown in the presence of CBS also attach firmly to the tissue culture flask and are difficult to detach using cell dissociation buffer.

FIG. 2 shows the flow cytometric dot plot of the cells cultured in the presence of FBS and CBS at passage 2. It is clear that >90% of the cells in both cultures at the first passage (P1) are CD45+ indicating a haematopoietic cell phenotype. The numbers of haematopoietic cells in both these cultures are not significantly different (p>0.2 by the paired T test). Therefore it is clear that CBS is as effective as FBS in supporting growth of adherent cells.

At the third passage (P3), these cells gradually loose the CD45 antigen (FIG. 2), indicating that they are converting to a non-haematopoietic phenotype. 60% of the cells cultured with FBS were CD45−, whereas 80% of the cells cultured with CBS exhibited a similar phenotype.

Comparison of the Kinetics CBS Vs FBS—Table and Picture

Cell Count of Cord Blood Suspension Cells Grown in FBS and CBS (FIG. 3)

| | Count in CBS | Count in FBS |
|---|---|---|
| | 2.5 | 2.6 |
| | 2 | 4 |
| | 3.6 | 4.32 |
| | 16 | 11.84 |
| | 0.5 | 0.48 |
| | 1.52 | 1.72 |
| | 8 | 1.1 |
| Mean | 4.87 | 3.72 |

Cell Count and Flow Cytometric Analysis of Adhered Cord Blood Cells Grown in FBS and CBS

| Sample No. | Count in CBS | Count in FBS | % CD133+/CD34−/CD45− (P1) | | % CD133+/CD34−/CD45− (P2) | |
|---|---|---|---|---|---|---|
| | | | CBS | FBS | CBS | FBS |
| 3580 | 0.25 | 0.5 | — | — | — | — |
| 3683 | 0.2 | 0.6 | 94.88 | 87.35 | | |
| 3722 | 0.25 | 0.65 | 93.33 | 92.5 | | |
| 3760 | 2.2 | 2.5 | 93.87 | 90.67 | 97.69 | 93.26 |
| 3711 | 0.4 | 1.5 | 93.79 | 91.94 | | |
| Means | 0.66 | 1.15 | 91.755 | 89.185 | | |

Transdifferentiation data: For the transdifferentiation, the differentiating agents tried were BHA, retinoic acid, DMSO or beta mercaptoethanol. Of these FBS in DMSO was found to be most effective in neural cell differentiation. After induction the adhered cells were fixed and 4% para formaldehyde and were stained with antibodies against Nestin and GFAP for detection by immunofluorescence. PE conjugated Goat anti-mouse antibody was used for detection of positive cells. The cells were counter stained with DAPI. FIGS. 4A and B.

The percentages of the differentiated cells (CD 34+/CD133+ differentiated cells) CBS CD133+ cells induced with BHA were stained with Mouse antihuman Nestin & GFAP antibodies. Of these cells 32% were positive for Nestin & 14% were positive for GFAP. FIG. 5A, B, C.

The viability of the cells was checked by viaprobe (7 Amini Actinomycin D). It is based on the dye exclusion property by the dead cells. More than 90% of the cells were viable. FIG. 6.

As noted heretofore, FIG. 1 illustrates the morphology of the adherent cells grown in the presence of FBS and CBS. In the first passage (P1) higher numbers of adherent cells are observed in the CBS culture. The FBS culture shows a higher number of rounded cells, but lower number of adherent cells. A similar difference is observed in cultures in the second passage (P2). The adherent cells in CBS also appear to be larger in size.

Differentiation of cord blood mononuclear cells to neural precursors: Mononuclear cells from umbilical cord blood were plated in neural cell proliferation medium as described above. The cultures were fed every 3-4 days and were allowed to proceed to 90% confluency, which was determined by visual examination of the flask under an invested microscope. The adherent cells were initially detached using cell dissociation buffer and seeded into the next passage. After 2 passages, these cells were then replated in 6 well chamber slides and induced with BHA for 5 hours in the absence of serum. The induced cells were then stained for the presence of neural markers like Nestin, Glial Fibrillar Acidic Protein (GFAP) and Neurofilament N (Neu-N). FIG. 3 shows the expression of these 3 markers on cultured cord blood mononuclear cells cultured in differentiation medium using BHA as the differentiating agent.

While there has been shown and described what is considered to be the preferred embodiments of the invention, it will be readily obvious to those skilled in this at that various changes and modifications may be made without departing from the scope of the invention.

The invention claimed is:

1. A method of growing umbilical cord mononuclear cells into neural precursors comprising the steps of:
   selecting CD34+, CD45+ and CD133+ cells from the mononuclear fraction of umbilical cord blood,
   growing these selected cells in a neural proliferation media comprising cord blood serum, and further growing the proliferated cells in a neural differentiation medium comprising one or more growth factors selected from BDNF, GDNF, NGF and FGF and neural differentiation agents selected from retinoic acid, BHA and DMSO, and cord blood serum to provide neural precursor cells.

2. The method according to claim 1, wherein the neural proliferation medium comprises DMEM/F12 supplemented with non-essential amino acids, glutamine, growth factors and human cord blood serum.

3. The method according to claim 1, wherein the neural differentiation media comprises DMEM/F12 supplemented with glutamine 2 mM, sodium bicarbonate 3 mM, EGF 20 ng/ml, bFGF 10 ng/ml and NGF 100 ng/ml, cord blood serum and a differentiating agent selected from retinoic acid, BHA and DMSO.

4. A method of using umbilical cord blood serum for growing the hematopoietic lymphocytic and neuroprogenitor cells of umbilical cord blood and transdifferentiating said cells into neural precursors comprising:
  a) collecting the umbilical cord blood;
  b) isolating the mononuclear cell fraction from the umbilical cord blood;
  c) sorting said mononuclear cell fraction using a magnetic cell separator to isolate the CD34+, CD45+ and CD133+ cells;
  d) culturing the sorted cells in a neural proliferation medium comprising cord blood serum until they are CD34−, CD45−, and CD133+ and
  e) further transdifferentiating the cultured −CD34−, CD45− and CD133+ cells in a neural differentiation medium comprising one or more growth factors selected from BDNF, GDNF, NGF and FGF and neural differentiation agents selected from retinoic acid, BHA and DMSO, and cord blood serum, thereby producing neural precursor cells.

5. The method as claimed in claim 4, wherein the neural differentiating medium comprises neural proliferation medium and retinoic acid.

6. The method as claimed in 4, wherein the neural proliferation medium comprises DMEM/F12 supplemented with growth factors and non-essential amino acids, glutamine and human cord blood serum.

7. The method as claimed in claim 4, wherein the umbilical cord blood is freshly obtained from umbilical cord or is cryopreserved umbilical cord blood.

8. The method as claimed in claim 4, wherein the umbilical cord blood is collected at the time of birth from pre-screened donors after separation of the baby from the donor.

9. The method as claimed in claim 4, including:
  collecting the blood and allowing the blood to clot at room temperature for a period between 8-16 hours and transporting the blood to a processing area;
  centrifuging the blood at 1000 g in a blood bag centrifuge and collecting clear serum and placement into sterile containers;
  testing the serum for sterility by microbiological assay for aerobic or anaerobic microorganisms; and
  inactivating the complement by maintaining sera at 56 degrees C. for ½ hour.

* * * * *